US 6,242,467 B1
(12) United States Patent
Faller

(10) Patent No.: US 6,242,467 B1
(45) Date of Patent: Jun. 5, 2001

(54) COMPOUNDS

(75) Inventor: Andrew Faller, Epping (GB)

(73) Assignee: SmithKline Beecham p.l.c., Brentford (GB)

(*) Notice: Subject to any disclaimer, the term of this patent is extended or adjusted under 35 U.S.C. 154(b) by 0 days.

(21) Appl. No.: 09/381,405

(22) PCT Filed: Mar. 16, 1998

(86) PCT No.: PCT/EP98/01766

§ 371 Date: Sep. 17, 1999

§ 102(e) Date: Sep. 17, 1999

(87) PCT Pub. No.: WO98/42659

PCT Pub. Date: Oct. 1, 1998

(30) Foreign Application Priority Data

Mar. 26, 1997 (GB) .................................................. 9706255

(51) Int. Cl.$^7$ .......................... A61K 31/44; A61K 31/19; C07C 259/00; C07D 409/00
(52) U.S. Cl. .......................... 514/336; 514/575; 562/625; 546/280.4
(58) Field of Search ............................. 546/278.4, 280.4; 514/336, 575; 562/625

(56) References Cited

FOREIGN PATENT DOCUMENTS

| 0 606 046 | 7/1994 | (EP) | C07D/213/42 |
|---|---|---|---|
| 0 757 984 | 2/1997 | (EP) . | |
| WO95 35276 | 12/1995 | (WO) | C07D/311/19 |
| WO96 02240 | 2/1996 | (WO) . | |
| WO 9705865 * | 2/1997 | (WO) . | |
| WO97 05865 | 2/1997 | (WO) | A61K/31/215 |
| WO97 44315 | 11/1997 | (WO) | C07C/311/19 |
| WO98 09934 | 3/1998 | (WO) | C07C/35/38 |

OTHER PUBLICATIONS

Chemical Abstracts Service, Columbus Ohio, US STN, Accession No. 70:88228, XP002074847.
Chemical Abstracts Service, Columbus Ohio, US STN, Accession No. 112:179786, XP002074848.

* cited by examiner

Primary Examiner—John Kight
Assistant Examiner—Binta Robinson
(74) Attorney, Agent, or Firm—Soma G. Simon; William T. King; Charles M. Kinzig

(57) ABSTRACT

Compounds of formula (I) wherein R is hydroxy, hydrogen, alkenyl, alkynyl or aryl, and R1 is aryl or heteroaryl, are useful in the treatment and prophylaxis of conditions mediated by CD23 or TNF.

9 Claims, No Drawings

COMPOUNDS

This application is a §371 application of PCT/EP98/01766 filed on Mar. 16, 1998.

This invention relates to novel inhibitors of the formation of soluble human CD23 and their use in the treatment of conditions associated with excess production of soluble CD23 (s-CD23) such as autoimmune disease and allergy.

CD23 (the low affinity IgE receptor FceRII, Blast 2), is a 45 kDa type II integral protein expressed on the surface of a variety of mature cells, including B and T lymphocytes, macrophages, natural killer cells, Langerhans cells, monocytes and platelets (Delespesse et al, *Adv Immunol*, 49 [1991] 149–191). There is also a CD23-like molecule on eosinophils (Grangette et al, *J Immunol*, 143 [1989] 3580–3588). CD23 has been implicated in the regulation of the immune response (Delespesse et al, *Immunol Rev*, 125 [1992] 77–97). Human CD23 exists as two differentially regulated isoforms, a and b, which differ only in the amino acids at the intracellular N-terminus (Yokota et al, *Cell*, 55 [1988] 611–618). In man the constitutive a isoform is found only on B-lymphocytes, whereas type b, inducible by IL4, is found on all cells capable of expressing CD23.

Intact, cell bound CD23 (i-CD23) is known to undergo cleavage from the cell surface leading to the formation of a number of well-defined soluble fragments (s-CD23), which are produced as a result of a complex sequence of proteolytic events, the mechanism of which is still poorly understood (Bourget et al *J Biol Chem*, 269 [1994] 6927–6930). Although not yet proven, it is postulated that the major soluble fragments (Mr 37, 33, 29 and 25 kDa) of these proteolytic events, all of which retain the C-terminal lectin domain common to i-CD23, occur sequentially via initial formation of the 37 kDa fragment (Letellier et al,*J Exp Med*, 172 [1990] 693–700). An alternative intracellular cleavage pathway leads to a stable 16 kDa fragment differing in the C-terminal domain from i-CD23 (Grenier-Brosette et al,*Eur J Immunol*, 22 [1992] 1573–1577).

Several activities have been ascribed to membrane bound i-CD23 in humans, all of which have been shown to play a role in IgE regulation. Particular activities include: a) antigen presentation, b) IgE mediated eosinophil cytotoxicity, c) B cell homing to germinal centres of lymph nodes and spleen, and d) downregulation of IgE synthesis (Delespesse et al, *Adv Immunol*, 49, [1991] 149–191). The three higher molecular weight soluble CD23 fragments (Mr 37, 33 and 29 kDa) have multifunctional cytokine properties which appear to play a major role in IgE production. Thus, the excessive formation of s-CD23 has been implicated in the overproduction of IgE, the hallmark of allergic diseases such as extrinsic asthma, rhinitis, allergic conjuctivitis, eczema, atopic dermatitis and anaphylaxis (Sutton and Gould, *Nature*, 366, [1993] 421–428).

Other biological activities attributed to s-CD23 include the stimulation of B cell growth and the induction of the release of mediators from monocytes. Thus, elevated levels of s-CD23 have been observed in the serum of patients having B-chronic lymphocytic leukaemia (Sarfati et al, *Blood*, 71 [1988] 94–98) and in the synovial fluids of patients with rheumatoid arthritis (Chomarat et al, *Arthritis and Rheumatism*, 36 [1993] 234–242). That there is a role for CD23 in inflammation is suggested by a number of sources. First, sCD23 has been reported to bind to extracellular receptors which when activated are involved in cell-mediated events of inflammation. Thus, sCD23 is reported to directly activate monocyte TNF, IL-1, and IL-6 release (Armant et al, vol 180, J.Exp. Med., 1005–1011 (1994)). CD23 has been reported to interact with the B2-integrin adhesion molecules, CD11b and CD11c on monocyte/macrophage (S. Lecoanet-Henchoz et al, Immunity, vol 3; 119–125 (1995)) which trigger $NO_2^-$, hydrogen peroxide and cytokine (IL-1, IL-6, and TNF) release. Finally, IL-4 or IFN induce the expression of CD23 and its release as sCD23 by human monocytes. Ligation of the membrane bound CD23 receptor with IgE/anti-IgE immune complexes or anti CD23 mAb activates cAMP and IL-6 production and thromboxane B2 formation, demonstrating a receptor-mediated role of CD23 in inflammation.

Because of these various properties of CD23, compounds which inhibit the formation of s-CD23 should have twofold actions of a) enhancing negative feedback inhibition of IgE synthesis by maintaining levels of i-CD23 on the surface of B cells, and b) inhibiting the immunostimulatory cytokine activities of higher molecular weight soluble fragments (Mr 37, 33 and 29 kDa) of s-CD23. In addition, inhibition of CD23 cleavage should mitigate sCD23-induced monocyte activation and mediator formation, thereby reducing the inflammatory response.

TNFα is a pro-inflammatory cytokine which is released from stimulated cells by specific cleavage of a 76-amino acid signal sequence in the inactive precursor to generate the mature form. The cleavage of TNFα has been reported to be carried out by a metalloprotease (Gearing, A. J. H. et al, (1994) Nature 370, 555–557; McGeehan, G. M. et al, (1994) Nature 370, 558–561; Mohler, K. M. et al, (1994) Nature 370, 218–220). Compounds reported to inhibit the cleavage of TNFα by the TNF processing enzyme can be broadly described as matrix metalloprotease inhibitors, particularly of the hydroxamic acid class.

TNFα is induced in a variety of cell types in response to bacteria, endotoxin, various viruses and parasites, so that one physiological function ascribed to TNFα is a contribution to the inflammatory response to acute infection by bacteria, parasites, etc (Dinarelo, Calif. (1992) Immunol. 4, 133–145). Overproduction of TNFα has been implicated in disease states such as rheumatoid arthritis, septic shock, Crohn's disease and cachexia (Dinarello, 1992). Inhibition of processing of TNFα to the mature, active form would therefore be beneficial in the treatment of these inflammatory disorders. TNFα may also contribute to the destruction of tissue in autoimmune disease although it is not an initiating factor in these diseases. Confirming the importance of TNFα in rheumatoid arthritis, TNFα antibodies have been shown to reduce the severity of disease in short term studies in rheumatoid arhritis models (Elliott, M. J., et al (1993) Arthrit. Rheum. 12, 1681–1690; Elliott et al (1994) Lancet 344, 1125–1127).

According to the present invention, there is provided a compound of formula (I):

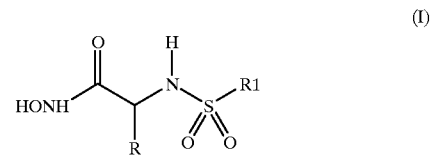

wherein R is hydroxy, hydrogen, alkenyl, alkynyl or aryl, and R1 is aryl or heteroaryl.

Alkyl, alkenyl and alkynyl groups referred to herein include straight and branched groups containing up to six carbon atoms and are optionally substituted by one or more groups selected from the group consisting of aryl, heterocyclyl, $(C_{1-6})$alkylthio, $(C_{2-6})$alkenylthio, $(C_{2-6})$ alkynylthio, arylthio, heterocyclylthio, $(C_{1-6})$alkoxy, aryl $(C_{1-6})$alkoxy, aryl$(C_{1-6})$alkylthio, amino, mono- or di-$(C_{1-6})$ alkylamino, cycloalkyl, cycloalkenyl, carboxy and esters thereof, hydroxy, and halogen.

Cycloalkyl and cycloalkenyl groups referred to herein include groups having between three and eight ring carbon atoms and are optionally substituted as described hereinabove for alkyl, alkenyl and allynyl groups.

When used herein, the term "aryl" includes phenyl and naphthyl such as 2-naphthyl. Suitably any aryl group, including phenyl and naphthyl, may be optionally substituted by up to five, preferably up to three substituents. Suitable substituents include halogen, $(C_{1-6})$alkyl, aryl$(C_{1-6})$alkyl, $(C_{1-6})$alkoxy, $(C_{1-6})$alkoxy$(C_{1-6})$alkyl, halo$(C_{1-6})$alkyl hydroxy, nitro, amino, mono- and di-N-$(C_{1-6})$ alkylamino, acylamino, acyloxy, carboxy, carboxy salts, carboxy esters, carbamoyl, mono- and di-N-$(C_{1-6})$ alkylcarbamoyl, $(C_{1-6})$alkoxycarbonyl, aryloxycarbonyl, ureido, guanidino, sulphonylamino, aminosulphonyl, $(C_{1-6})$ alkylthio, $(C_{1-6})$alkyl sulphinyl $(C_{1-6})$alkylsulphonyl, heterocyclyl and heterocyclyl $(C_{1-6})$alkyl. In addition, two adjacent ring carbon atoms may be linked by a $(C_{3-5})$ alkylene chain, to form a carbocyclic ring. Thus, the term "aryl" includes single and fused rings, of which at least one is aromatic, which rings may be unsubstituted or substituted by, for example, up to three substituents as set out above. Each ring suitably has from 4 to 7, preferably 5 or 6, ring atoms.

When used herein the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each ring suitably has from 4 to 7, preferably 5 or 6, ring atoms. A fused heterocyclic ring system may include carbocyclic rings and need include only one heterocyclic ring.

When used herein the term "heteroaryl" suitably includes any heterocyclyl group which incorporates at least one aromatic ring (heterocyclic or carbocyclic).

Preferably a substituent for a heterocyclyl group is selected from halogen, $(C_{1-6})$alkyl, aryl$(C_{1-6})$alkyl, $(C_{1-6})$ alkoxy, $(C_{1-6})$alkoxy$(C_{1-6})$alkyl, halo$(C_{1-6})$alkyl, hydroxy, amino, mono- and di-N-$(C_{1-6})$alkyl-amino, acylamino, carboxy salts, carboxy esters, carbamoyl, mono- and di-N-$(C_{1-6})$alkylcarbonyl, aryloxycarbonyl, $(C_{1-6})$alkoxycarbonyl$(C_{1-6})$alkyl, aryl, oxy groups, ureido, guanidino, sulphonylamino, aminosulphonyl, $(C_{1-6})$alkylthio, $(C_{1-6})$ alkylsulphinyl, $(C_{1-6})$alkylsulphonyl, heterocyclyl and heterocyclyl$(C_{1-6})$alkyl.

In a particular aspect of the invention, R is isopropyl; isobutyl, or 4-(uffluoroacetamido)butyl, and/or R1 is a phenyl group, optionally substituted, for example by methoxy, such as 4-methoxyphenyl, or a fused aromatic group such as 2-naphthyl, or 5-(2-pyridyl)thiophen-2-yl.

According to a further aspect, the present invention provides the use of a compound of formula (I) for the production of a medicament for the treatment or prophylaxis of disorders such as allergy, inflammatory disorders, and autoimmune disease, in which the overproduction of s-CD23 is implicated.

In a further aspect the invention provides a method for the treatment or prophylaxis of disorders such as allergy, inflammatory disorders, and autoimmune disease, in which the overproduction of s-CD23 is implicated, which method comprises the administration of a compound of formula (I), to a human or non-human mammal in need thereof.

The invention also provides a pharmaceutical composition for the treatment or prophylaxis of disorders such as allergy, inflammatory disorders, and autoimmune disease, in which the overproduction of s-CD23 is implicated which comprises a compound of formula (I) and optionally a pharmaceutically acceptable carrier therefor.

Particular inflammatory disorders include CNS disorders such as Alzheimers disease, multiple sclerosis, and multi-infarct dementia, as well as the inflammation mediated sequelae of stroke and head trauma.

According to a further aspect, the present invention provides the use of a compound of formula (I) for the production of a medicament for the treatment or prophylaxis of conditions mediated by TNF, including, but not limited to, inflammation, fever, cardiovascular effects, haemorrhage, coagulation and acute phase response, cachexia and anorexia, acute infections, shock states, graft versus host reactions and autoimmune disease.

In a further aspect the invention provides a method for the treatment or prophylaxis of conditions mediated by TNF, which method comprises the administration of a compound of formula (I), to a human or non-human mammal in need thereof.

The invention also provides a pharmaceutical composition for the treatment or prophylaxis of conditions mediated by TNF, which comprises a compound of formula (I) and optionally a pharmaceutically acceptable carrier therefor.

The present inventors have surprisingly found that the compounds of the invention are potent and selective inhibitors of both CD23 processing and TNF processing, whilst having little or no activity as inhibitors of matrix metalloproteases. A further aspect of the invention thus provides the use of a TNF processing inhibitor for the production of a medicament for the treatment or prophylaxis of conditions mediated by sCD23, characterised in that the TNF processing inhibitor is not an inhibitor of matrix metalloprotease.

It is to be understood that the pharmaceutically acceptable salts, solvates and other pharmaceutically acceptable derivatives of the compound of formula (I) are also included in the present invention.

Salts of compounds of formula (I) include for example acid addition salts derived from inorganic or organic acids, such as hydrochlorides, hydrobromides, hydroiodides, p-toluenesulphonates, phosphates, sulphates, acetates, trifluoroacetates, propionates, citrates, maleates, fumarates, malonates, succinates, lactates, oxalates, tartrates and benzoates.

Salts may also be formed with bases. Such salts include salts derived from inorganic or organic bases, for example alkali metal salts such as sodium or potassium salts, and organic amine salts such as morpholine, piperidine, dimethylamine or diethylamine salts.

The compounds of the invention may be prepared by use of any appropriate conventional method, for example by analogy with the methods disclosed in patent publication EP-A-0 606 046.

Accordingly, a further aspect of the invention provides a process for preparing a compound of formula (I) as defined hereinabove, which process comprises:

(a) deprotecting a compound of formula (II):

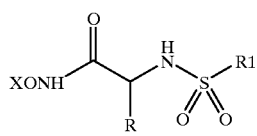

(II)

wherein R and R1 are as defined hereinabove, and X is a protecting group such as benzyl or trimethylsilyl or (b) reacting a compound of formula (III):

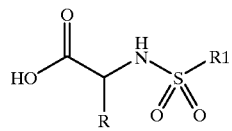

(III)

wherein R and R1 are as defined hereinabove, with hydroxylamine or a salt thereof, or (c) converting a compound of formula (I) to a different compound of formula (I) as defined hereinabove.

Compounds of formula (II) are novel and form a further aspect of the invention.

Compounds of formula (II) can be prepared from compounds of formula (III) by reaction with a protected hydroxylamine. Compounds of formula (III) can be prepared by hydrolysis of a compound of formula (IV):

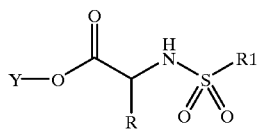

(IV)

wherein R and R1 are as defined hereinabove, and Y is a protecting group such as t-butyl.

Suitable protecting groups for a hydroxamic acid are well known in the art and include benzyl, trimethylsilyl, t-butyl and t-butyldimethylsilyl.

Suitable protecting groups for a carboxylic acid are well known in the art and include t-butyl, benzyl and methyl.

Compounds of formula (IV) can be prepared by reacting a compound of formula (V):

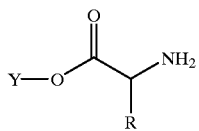

(V)

wherein R and Y are as defined hereinabove, with a compound of formula $R^1SO_3H$, wherein R1 is as defined hereinabove, or an activated derivative thereof, such as an arylsulfonyl chloride.

The starting materials and other reagents are available commercially or can be synthesised by well-known and conventional methods.

The isomers, including stereoisomers, of the compounds of the present invention may be prepared as mixtures of such isomers or as individual isomers. The individual isomers may be prepared by any appropriate method, for example individual stereoisomers may be prepared by stereospecific chemical synthesis starting from chiral substrates or by separating mixtures of diastereoisomers using known methods. In a preferred aspect, the invention provides compounds of formula (IA):

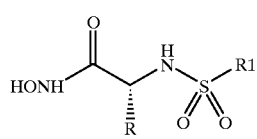

(1A)

It is preferred that the compounds are isolated in substantially pure form.

As stated herein an inhibitor of the formation of soluble human CD23 has useful medical properties. Preferably the active compounds are administered as pharmaceutically acceptable compositions.

The compositions are preferably adapted for oral administration. However, they may be adapted for other modes of administration, for example in the form of a spray, aerosol or other conventional method for inhalation, for treating respiratory tract disorders; or parenteral administration for patients suffering from heart failure. Other alternative modes of administration include sublingual or transdermal administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns for example diameters in the range of 1–50 microns, 1–10 microns or 1–5 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

The compositions may contain from 0.1% to 99% by weight, preferably from 10–60% by weight, of the active material, depending upon the method of administration. A preferred range for inhaled administration is 10–99%, especially 60–99%, for example 90, 95 or 99%.

Microfine powder formulations may suitably be administered in an aerosol as a metered dose or by means of a suitable breath-activated device.

Suitable metered dose aerosol formulations comprise conventional propellants, cosolvents, such as ethanol, surfactants such as oleyl alcohol, lubricants such as oleyl alcohol, desiccants such as calcium sulphate and density modifiers such as sodium chloride.

Suitable solutions for a nebulizer are isotonic sterilised solutions, optionally buffered, at for example between pH 4–7, containing up to 20 mg/ml of compound but more generally 0.1 to 10 mg/ml, for use with standard nebulisation equipment.

An effective amount will depend on the relative efficacy of the compounds of the present invention, the severity of the disorder being treated and the weight of the sufferer. Suitably, a unit dose form of a composition of the invention may contain from 0.1 to 1000 mg of a compound of the invention (0.001 to 10 mg via inhalation) and more usually from 1 to 500 mg, for example 1 to 25 or 5 to 500 mg. Such compositions may be administered from 1 to 6 times a day, more usually from 2 to 4 times a day, in a manner such that the daily dose is from 1 mg to 1 g for a 70 kg human adult and more particularly from 5 to 500 mg. That is in the range of about $1.4 \times 10^{-2}$ mg/kg/day to 14 mg/kg/day and more particularly in the range of about $7 \times 10^{-2}$ mg/kg/day to 7 mg/kg/day.

The following examples illustrate the invention but do not limit it in any way.

EXAMPLE 1

2-(R)N-Hydroxy-[(4-Metioxybenzene)sulfonyl]amino-3-methylbutyramide

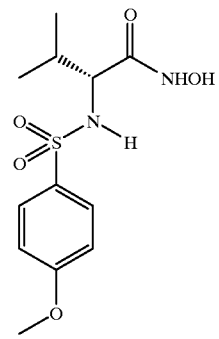

a) 2-(R)-N-[(4-methoxybenzene)sulfonyl]valine

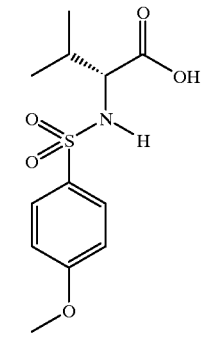

To a solution on D-valie (10 g, 85.4 mmol) in 1,4-dioxan (200 ml) and water (100 ml) at 0° C. was added triethylamine (59 ml, 427 mmol) followed by 4-methoxybenzene sulfonylchioride (21 g, 102 mmol). The solution was allowed to warm to ambient temperature and stiffed for 2 days. The organic solvent was removed at reduced pressure and the residue made alkaline with sodium bicarbonate. This solution was extracted with ethyl acetate, then acidified using 2N HCl and extracted with ethyl acetate (×2). These extracts were dried and the solvent removed under reduced pressure to give the title compound (22 g, 90%) as a white solid.

1H nmr ($d_6$-DMSO) 0.74 (6H, d, J=6.9 Hz), 1.68–1.99 (1H, m), 3.20–3.28 (1H, m), 3.82 (3H, s), 7.04 (2H, d, J=9 Hz), 7.68 (2H, d, J=9 Hz), 7.66–7.73 (1H, br), 10.7 (1H,br.)

b) 2-(R)-N-Hydroxy-[(4Methoxybenzene)sulfonyl]amino-3-methylbutyramide

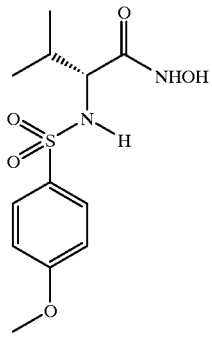

To a solution of 2-(R)-N-[(4-methoxybenzene)sulfonyl] valine (1 g, 3.5 mmol) in DMF (72 ml) was added 1-hydroxy-7-azabenzotriazole (HOAt, 629 mg, 4.5 mmol), 1-(3-dimethylaminopropyl)3-ethylcarbodiimide hydrochloride (DEC, 879 mg, 4.5 mmol), hydroxylamine hydrochloride (278 mg, 3.8 mmol) and N-methylmorpholine (0.5 ml, 3.8 mmol) and the solution stirred for 18 h. The solvent was removed under reduced pressure and the residue dissolved in ethyl acetate then washed with citric acid (10% solution), sodium bicarbonate (satd) and brine. The solution was dried and concentrated under reduced pressure to give a yellow foam which was triturated with diethyl ether to yield a white solid (0.5 g, 48%)

MH$^+$ 303, MNa$^+$ 325; 1H nmr (d$_6$-DMSO) 0.73 (6H, d, J=6.9 Hz), 1.68–1.99 (1H, m), 3.21–3.28 (1H, m), 3.82 (3H, s), 7.04 (2H, d, J=8.8 Hz), 7. (2H, d, J=8.8 Hz), 7.66–7.73 (1H, br), 8.77 (1H, s), 10.47 (1H, s).

EXAMPLE 2

2-(R)-N-Hydroxy-[(2-naphthyl)sulfonyl]andno-3-methiylbutyraniide

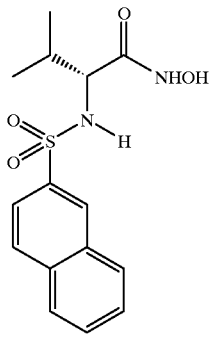

This was prepared from 2-(R)-N-[(4-methoxybenzene)sulfonyl]valine and 2-naphthylsulfonylchloride by the procedure of example 1b (45%) as a cream solid.

MNH$_4^+$ 340; 1H nmr (d$_6$-DMSO) 0.71–0.76 (6H,m), 1.74–1.81 (1H, m), 3.27–3.36 (1H, m), 7.63–7.68 (2H, m), 7.80 (1H, d, J=8.5 Hz), 8.01–8.12 (4H, m), 8.37 (1H, s), 8.75 (1H, s), 10.51 (1H, s).

EXAMPLE 3 a) N((5-(2-pyridyl)thiophen-2-ylsulfonyl)-(R)-leucine

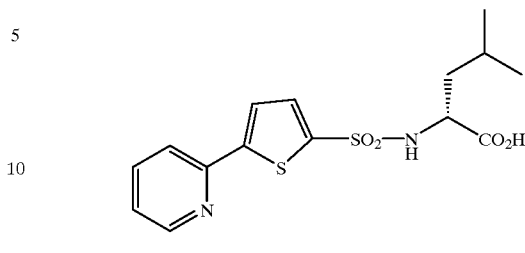

The title compound was prepared as in Example 1.

NMR: (DMSO-d6) δ 0.80 (3H, d, J=6.5 Hz), 0.87 (3H, d, J=6.5 Hz), 1.46 (2H, m), 1.66 (1H, septet, J=6.3 Hz), 3.79 (1H, m), 7.41 (1H, m), 7.59 (1H, d, J=4 Hz), 7.84 (1H, d, J=4 Hz), 7.94 (1H, m), 8.07 (1H, d, J=8 Hz), 8.45 (1H, v. br. s), 8.62 (1H, d, J=4.2 Hz); MS: (M+H)=355.

b) N-hydroxy-Nα((5-(2-pyridylthiophen-2-yisulfonyl)-(R)-leucinamide

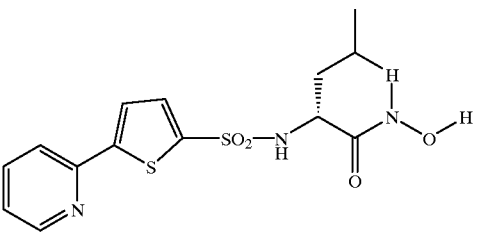

The title compound was prepared as in Example 1

NMR: (DMSO-d6) δ 0.70 (1H, d, J=6.4 Hz), 0.78 (1H, d, J=6.4 Hz), 1.33 (2H, m), 1.47 (1H, septet, J=6.4 Hz), 3.65 (1H, m), 7.38 (1H, m), 7.54 (1H, d, J=4 Hz), 7.80 (1H, d, J=4 Hz), 7.90 (1H, m), 8.02 (1H, d, J=7.9 Hz), 8.30 (1H, br., d), 8.59 (1H, d, J=4.2 Hz), 8.87 (1H, s), 10.72 (1H, s); MS: (M+H)=370.

EXAMPLE 4 a) Nε-tertbutoxycarbonyl-Nα(5-(2-pyridyl)thiophen-2-ylsulfonyl)-(R)-lysine

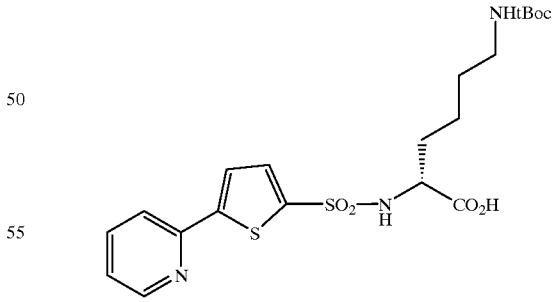

The title compound was prepared as in Example 1

NMR: (DMSO-d6) δ 1.22–1.42 (4H, br., m), 1.41 (9H, s), 1.50–1.75 (2H, br., m), 2.88 (2H, br. q, J~6 Hz), 3.79 (1H, m), 6.76 (1H, br., t), 7.44 (1H, m), 7.61 (1H, d, J=4 Hz), 7.86 (1H, d, J=4 Hz), 7.96 (1H, m), 8.08 (1H, d, J=8 Hz), 8.64 (1H, d J=4.2 Hz); MS: (M+H)=470.

b) Nε-tertbutoxycarbonyl-N-hydroxy-Nα-(5-(2-pyridyl)thiophen-2-ylsulfonyl)(R)-lysinamide

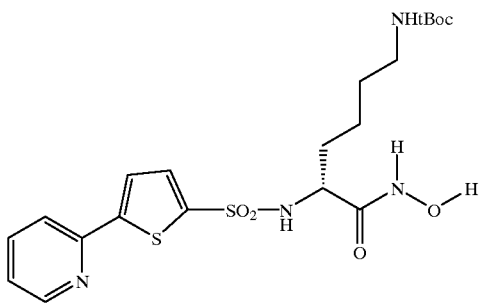

The title compound was prepared as in Example 1
NMR: (DMSO-d6) δ 1.0–1.36 (4H, br., m), 1.36–1.56 (2H, br., m), 1.36 (9H, s). 2.79 (2H, br. q, J~6 Hz), 3.67 (1H, br. m), 6.70 (1H, br., t), 7.40 (1H, m), 7.56 (1H, d, J=4 Hz), 7.82 (1H, d, J=4 Hz), 7.93 (1H, m), 8.04 (1H, d, J=8 Hz), 8.33 (1H, d, J~7 Hz, SO₂NH), 8.60 (1H, d, J=4.2 Hz), 8.89 (1H, s), 10.64 (1H, s); MS: (M+H)=485.

c) N-hydroxy-Nα(5-(2-pyridyl)thiophen-2-ylsulfonyl)-(R)-lysinamide trifluoroacetate salt

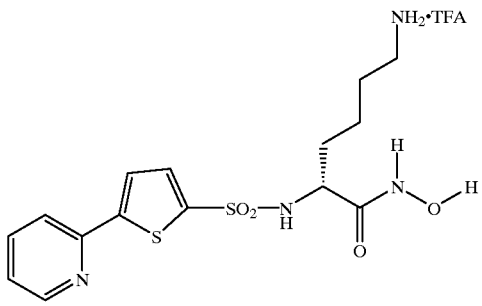

The title compound was prepared by treatment of Nε-tertbutoxycarbonyl-N-hydroxy-Nα-(5-(2-pyridyl)thiophen-2-yisulfonyl)-(R)-lysinamide with trfluoracetic acid: dichloromethane (1:1) until all starting material had disappeared (tlc), then removal of volatiles.

NMR: (DMSO-d6) δ 1.1–1.65 (6H, br., m), 2.75 (2H, m), 3.71 (1H, br., q), 7.25 (1H, m), 7.45 (1H, m), 7.61 (1H, d, J=4 Hz), 7.68 (~2H, br., s), 7.88 (1H, d, J=4 Hz), 7.98 (1H, m), 8.11 (1H, d, J=8 Hz), 8.43 (1H, d, J=8.5 Hz), 8.65 (1H, d, J=4.2 Hz), 10.75 (1H, s); MS: (M+H)=385.

What is claimed is:

1. A compound of formula (I):

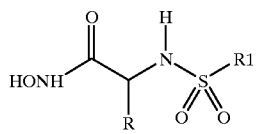

wherein R is hydroxy, hydrogen, isopropyl; isobutyl, or 4-(trifluoroacetamido)butyl, alkenyl, alkynyl or aryl, and R1 is 2-naphthyl, 4-methoxyphenyl or 5-(2-pyridyl)thiophen-2-yl.

2. A compound selected from the group consisting of
2-(R)-N-Hydroxy-[(4-Methoxybenzene)sulfonyl]amino-3-methylbutyramide
2-(R)-N-Hydroxy-[(2-naphthyl)sulfonyl]amino-3-methylbutyramide
N-hydroxy-Nα((5-(2-pyridyl)thiophen-2-ylsulfonyl)-(R)-leucinamide
N-hydroxy-Nα(5-(2-pyridyl)thiophen-2-ylsulfonyl)-(R)-lysinamide trifluoroacetate salt.

3. A compound of formula (II):

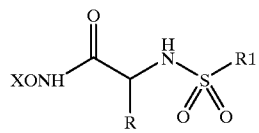

wherein R and R1 are as defined in claim 1, and X is a protecting group.

4. A pharmaceutical composition for the treatment or prophylaxis of disorders in which the overproduction of s-CD23 is implicated which comprises a compound according to claim 1 and optionally a pharmaceutically acceptable carrier therefor.

5. A pharmaceutical composition for the treatment or prophylaxis of conditions mediated by TNF, which comprises a compound according to claim 1 and optionally a pharmaceutically acceptable carrier therefor.

6. A pharmaceutical composition comprising a compound of claim 1 and a pharmaceutical acceptable carrier thereof for the treatment or prophylaxis of conditions mediated by sCD23, which comprises a TNF processing inhibitor, characterised in that the TNF processing inhibitor is not an inhibitor of matrix metalloprotease.

7. A method for the treatment or prophylaxis of disorders in which the overproduction of s-CD23 is implicated, which method comprises the administration of a compound according to claim 1 to a human or non-human mammal in need thereof.

8. A method for the treatment or prophylaxis of conditions mediated by TNF, which method comprises the administration of a compound according to claim 1 to a human or non-human mammal in need thereof.

9. A process for preparing a compound according to claim 1 which process comprises:

(a) deprotecting a compound of formula (II):

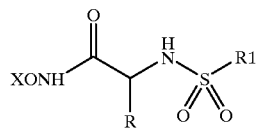

wherein R is hydroxy, hydrogen, isopropyl, isobutyl, or 4-(trifluoroacetamido)butyl, alkenyl, alkynyl, or aryl and R1 is 2-naphthyl, 4-methoxyphenyl or 5-(2-pyridyl)thiophen-2-yl in claim 1, and X is a protecting group, or (b) reacting a compound of formula (III):

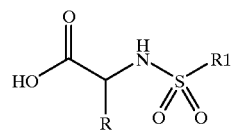

wherein R is hydroxy, hydrogen, isopropyl, isobutyl, or 4-(trifluoroacetamido)butyl, alkenyl, alkynyl, or aryl and R1 is 2-naphthyl, 4-methoxyphenyl or 5-(2-pyridyl)thiophen-2-yl in claim 1, with hydroxylamine or a salt thereof.

* * * * *